United States Patent [19]
Korsah et al.

[11] Patent Number: 6,044,332
[45] Date of Patent: Mar. 28, 2000

[54] SURFACE ACOUSTIC WAVE HARMONIC ANALYSIS

[75] Inventors: Kofi Korsah; William B. Dress, both of Knoxville; Cheng Yu Ma, Oak Ridge; Michael R. Moore, Corryton, all of Tenn.

[73] Assignee: Lockheed Martin Energy Research Corporation, Oak Ridge, Tenn.

[21] Appl. No.: 09/060,841

[22] Filed: Apr. 15, 1998

[51] Int. Cl.[7] .......................... G01N 30/00; G01R 23/167
[52] U.S. Cl. ...................... 702/76; 73/24.06; 324/76.19; 324/76.23; 324/76.24
[58] Field of Search ................................. 702/74, 75, 76, 702/77; 73/24.01, 24.03, 24.06; 324/76.44, 76.43, 76.42, 76.12, 76.19, 76.23, 76.24

[56] References Cited

U.S. PATENT DOCUMENTS

| | | | |
|---|---|---|---|
| 4,312,228 | 1/1982 | Wohltjen | 73/23.31 |
| 4,726,225 | 2/1988 | Brace et al. | 73/204.23 |
| 4,895,017 | 1/1990 | Pyke et al. | 73/24.06 |
| 4,947,677 | 8/1990 | Frye et al. | 73/38 |
| 5,076,094 | 12/1991 | Frye et al. | |
| 5,508,661 | 4/1996 | Keane et al. | 331/179 |
| 5,736,845 | 4/1998 | Kosuge | 324/76.23 |

OTHER PUBLICATIONS

M.S. Nieuwenhuizen and J.L.N. Harteveld, "A Surface Acoustic Wave Gas Sensor: Detection of Organophosphorus Compounds," *Sensors and Actuators* B 18–19 (1994) 502–505.

Corrine Dejous, et al., "A Surface Acoustic Wave Gas Sensor: Detection of Organophosphorus Compounds," *Sensors and Actuators* B 24–25 (1995) 58–61.

R.S. Falconer, A Versatile SAW–Based Sensor System for Investigating Gas–Sensitive Coatings, Sensors and Actuators B24–25 (1995) 54–57.

S. Rose Pehrsson, et al., "Detection of Hazardous Vapors Including Mixtures Using Pattern Recognition Analysis of Responses from Surface Acoustic Wave Devices," *Analytical Chemistry*, vol. 60, No. 24, 1988.

*Primary Examiner*—Marc S. Hoff
*Assistant Examiner*—Bryan Bui
*Attorney, Agent, or Firm*—Quarles & Brady LLP

[57] ABSTRACT

A method for sensing and analyzing data with surface acoustic wave (SAW) devices comprises the steps of: propagating a sampling signal at a fundamental frequency through a SAW device coated for selective adsorption; measuring at least one parameter of at least one higher order harmonic of the fundamental frequency sampling signal; exposing the coated SAW device to enable the selective adsorption; measuring the at least one parameter of the at least one higher order harmonic of the fundamental frequency sampling signal after the exposing step; comparing the measurements of the at least one parameter of the at least one higher order harmonic before and after the exposing step; and, deriving a result of the selective adsorption based upon the comparing step. The at least one parameter is harmonic power and harmonic frequency. The at least one higher order harmonic is one or more odd harmonics.

25 Claims, 2 Drawing Sheets

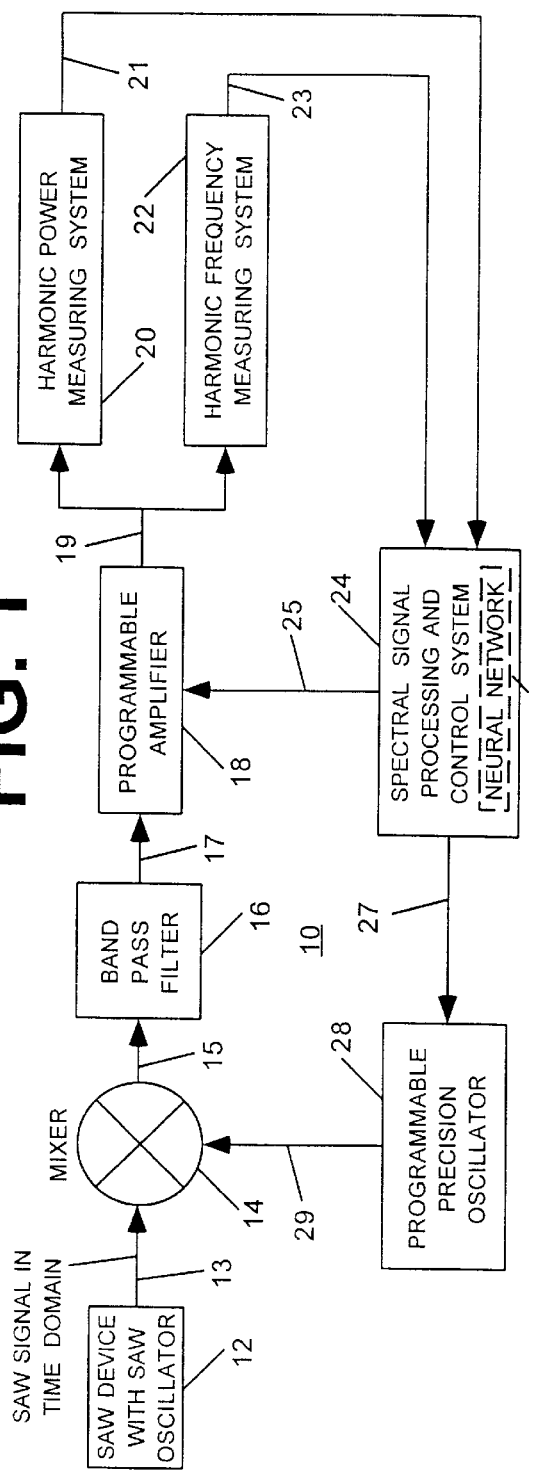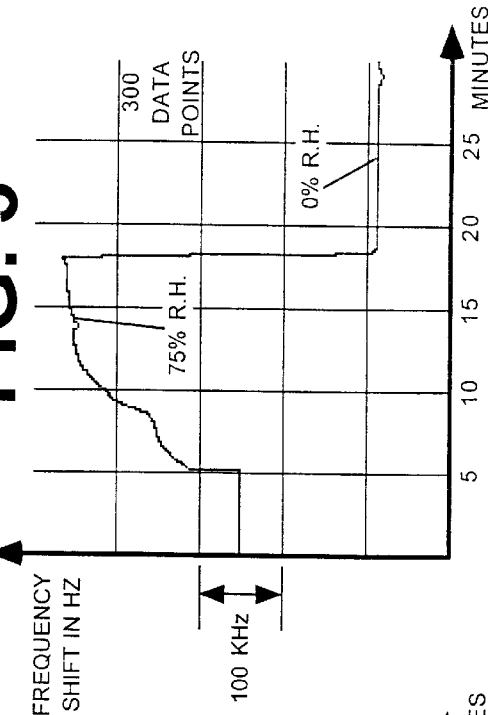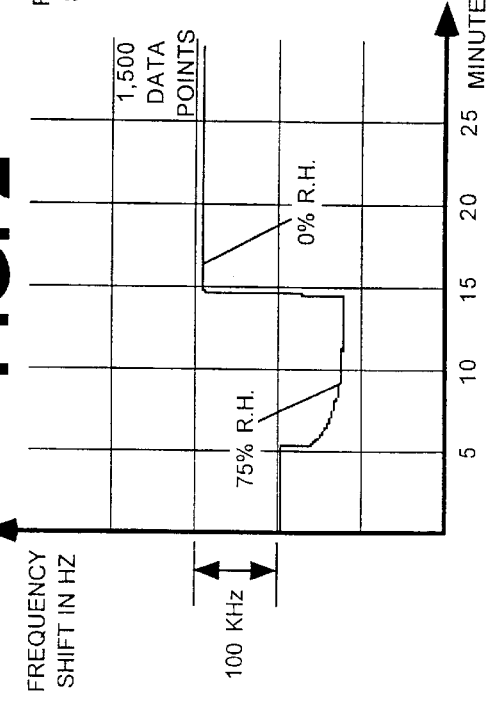

SURFACE ACOUSTIC WAVE HARMONIC ANALYSIS

BACKGROUND OF THE INVENTION

1. Field of the Invention

This invention relates to the field of chemical, biological agent and radiation sensors, and in particular, to such sensors embodied in surface acoustic wave devices.

2. Description of Related Art

Surface acoustic wave (SAW) devices are electronic components, embodied as filters, resonators, and delay lines exploiting surface acoustic waves in piezoelectric crystals. An interdigital transducer (IDT) converts an electronic signal into a surface acoustic wave which, propagating 100,000 times slower than electromagnetic waves, can deliver significant signal delays in the device. Signal filtering is performed by apodized IDT during electric to SAW signal conversion, or back conversion by another IDT. This is referred to as transversal filtering.

SAW devices can be used to detect intrinsic properties, and as such, are used as chemical, biological agent and radiation sensors and analyzers. As noted, a basic SAW device is a quartz crystal designed to support high-frequency acoustic oscillations. These oscillations are quite sensitive to surface effects. If the surface of a SAW device is provided with a coating which is attractive to a desired chemical or class of chemicals, for example, then such chemicals will tend to be adsorbed by the coating when in the presence of the SAW device. The difference between the fundamental frequency of the coated SAW device prior to adsorption of chemicals and after the adsorption of chemicals can be a reliable and accurate measure of the presence or concentration of the adsorbed chemical, although not both simultaneously. SAW devices with coatings which exhibit a preference for absorbing particular kinds of radiation, for example photo-conductivity or heating under the effects of ultra violet or infrared light, can be used as detectors for such radiation. The difference between the fundamental frequency before and after exposure to the radiation can produce a measurable shift in the fundamental frequency of the coated SAW device which can be a reliable and accurate measure of the presence or concentration of radiation, although not both simultaneously. SAW devices with coatings which adsorb and desorb (that is, release) chemicals or thermal energy, for example, as concentrations of the chemical or thermal energy rise and fall, can be used as continuous detectors.

Development of new chemical, biological agent and radiation sensors, and/or new methods of improving the sensitivity and detection limit of existing systems, are important areas of current research. The conventional method of measuring gas concentration using a SAW sensor is by measuring changes in only the fundamental frequency. For practical considerations, the majority of SAW gas sensors operate at frequencies below 300 MHz. The sensitivity of SAW devices is a function of the square of the operating frequency. Thus, although potentially more sensitive than other gas sensing methods, such as the use of infrared absorption spectra, these practical limitations restrict their actual sensitivity to many gases. In addition, the identification of a particular species from interfering gases by measuring a single parameter, that is frequency, is impossible. Attempts to solve this problem have conventionally been using an array of several sensors. However, in many cases false identification remains a problem.

Most publications and patents on SAW chemical sensors relate to the development of new polymer or conductive coatings for sensing particular gases of interest, or the use of sensor arrays to detect a particular gas of interest among interfering gases. However, their sensitivity relative to other methods such as those described above remains poor. U.S. Pat. No. 5,076,094 describes a method for identifying and quantifying absorbed chemical species by measuring changes in both the velocity and attenuation of the acoustic wave traveling through a thin film into which the chemical species is absorbed.

SUMMARY OF THE INVENTION

In accordance with the inventive arrangements, the problems of the prior art are overcome by operating a single SAW device sensor at its fundamental frequency, while extracting the gas concentration and/or other chemical identification information from higher harmonic frequencies and amplitudes. Extracting information from the harmonic of a SAW signal enables microwave frequency operation for gas detection, for example, without actually having to fabricate a device using submicron lithographic techniques or resorting to costly electron-beam lithography. Several significant advantages can achieved by extracting frequency, amplitude, and modulation characteristics from the Nth harmonic of the surface acoustic wave signal. The sensitivity of an acoustic wave gas sensor can be improved by a factor of N, as above. The number of sensors required for mixtures can be reduced by a factor of x, where x is the number of harmonic amplitudes and/or frequency variables measured. The gas detection limit of the chemical species of interest can be improved by a factor of at least two. A single sensor can provide both the identity and concentration of a chemical species. Another significant advantage of the inventive arrangements is that the methodology and related device sensors can always be used to optimize any SAW sensor device, independent of the fundamental operating frequency of the SAW device itself. Optimization includes, but is not limited to, increasing sensitivity, enhancing detection limits and increasing discrimination among interfering gases, or more generally, among interfering chemicals.

A method for sensing and analyzing data with surface acoustic wave (SAW) devices in accordance with an inventive arrangement comprises the steps of: propagating a sampling signal at a fundamental frequency through a SAW device coated for selective adsorption; measuring at least one parameter of at least one higher order harmonic of said fundamental frequency sampling signal; exposing said coated SAW device to enable said selective adsorption; measuring said at least one parameter of said at least one higher order harmonic of said fundamental frequency sampling signal after said exposing step; comparing said measurements of said at least one parameter of said at least one higher order harmonic before and after said exposing step; and, deriving a result of said selective adsorption based upon said comparing step.

The at least one parameter is advantageously harmonic power, harmonic frequency or both.

The at least one higher order harmonic is advantageously an odd-numbered harmonic, advantageously one or more of the 3rd, 5th and higher order harmonics.

When more than one harmonic is selected, the harmonics can advantageously be generated, measured and compared sequentially or simultaneously.

Automatic operation of the method can be advantageously implemented with a neural network.

The method can advantageously comprise the further step of calibrating signal detection such that prior to the exposing step, all harmonics selected for generation and measurement have an equal signal power level.

An apparatus for sensing and analyzing data with surface acoustic wave (SAW) devices, in accordance with another inventive arrangement, comprises: a SAW device configured for operation with a SAW oscillator and coated for selective adsorption; an harmonic signal oscillator for generating at least one higher order harmonic of said fundamental frequency of said SAW oscillator; a mixer for combining said at least one higher order harmonic and an output signal of said SAW device; a band-pass filter for said combined signal; a programmable amplifier for said band-pass filtered signal; a circuit for measuring at least one parameter of said amplified signal before and after said selective adsorption; an analyzer for comparing said measurements of said at least one parameter of said amplified signal before and after said selective adsorption, and deriving from said comparing a result of said selective adsorption.

The oscillator and said programmable amplifier are advantageously controlled by said analyzer.

The measuring circuit advantageously measures harmonic power, harmonic frequency or both.

The oscillator can advantageously generate at least two higher order odd harmonics of said fundamental frequency, each of which is measured before and after said selective adsorption, said analyzer deriving said result from a comparison of before and after measurements of said at least two higher order odd harmonics.

The at least two higher order odd harmonics can advantageously be generated and measured sequentially or simultaneously.

The analyzer can advantageously comprise a neural network.

Signal detection can be advantageously calibrated such that prior to the exposing step, all harmonics selected for generation and measurement have an equal signal power level.

BRIEF DESCRIPTION OF THE DRAWINGS

FIG. 1 is a block diagram of a surface acoustic wave harmonic signature analyzer in accordance with the inventive arrangements.

FIG. 2 is a graph of the frequency shifts from the fundamental frequency measured at the output of the oscillator in FIG. 1.

FIG. 3 is a graph of the frequency shifts of the third harmonic frequency measured at the output of the harmonic frequency measuring system in FIG. 1.

DETAILED DESCRIPTION OF THE PREFERRED EMBODIMENTS

Figure 4:
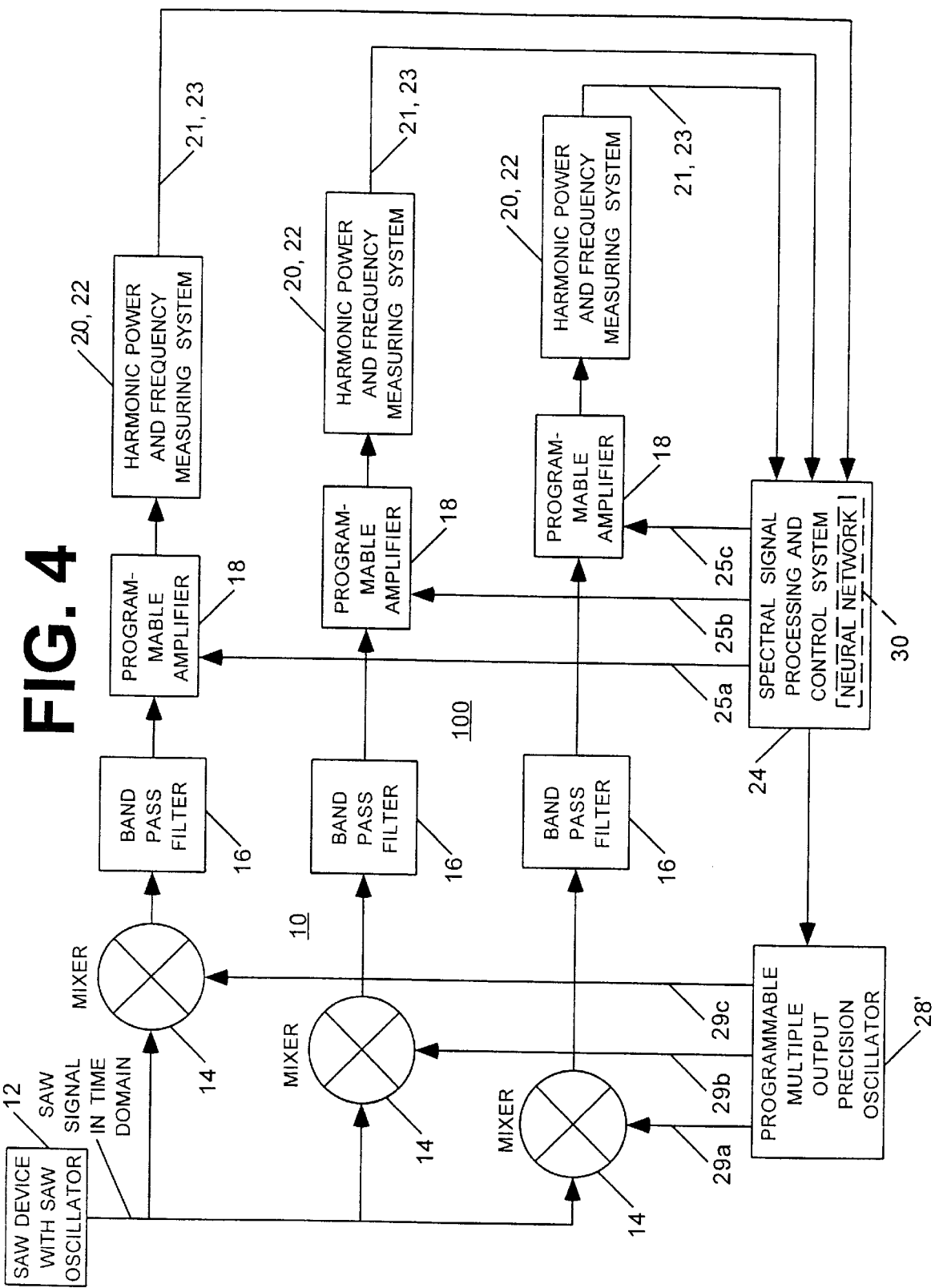
FIG. 4 is a block diagram of an alternative embodiment of a surface acoustic wave harmonic signature analyzer in accordance with the inventive arrangements.

The inventive arrangements are directed to methods and apparatus for surface acoustic wave harmonic analysis of chemicals, biological agents, radiation and other detectable phenomena. There are two principle aspects to the methods and apparatus of the inventive arrangements. A first aspect is extracting the Nth harmonic frequency from the SAW signal. Monitoring frequency changes of this higher harmonic provides the higher sensitivity. A second aspect is measuring the signal power of the 1st through the Nth harmonic from the frequency spectrum of the SAW signal. Monitoring the signal power in the individual harmonics, as well as the frequency shifts in the Nth harmonic, improves the discriminating ability among interfering gases, or more generally, interfering chemicals.

In an enhanced embodiment, a neural network based back-propagation algorithm that develops a harmonic signature from the above measurements to identify the chemical species and concentration can be used to facilitate automatic processing and recognition.

Odd-numbered harmonics are of particular interest in this context because, as can be shown, the interdigital transducers (IDT) of a SAW device excite harmonics at odd multiples of the synchronous or fundamental frequency.

FIG. 1 is a block diagram of a SAW harmonic signature analyzer 10 in accordance with the inventive arrangements. Although the various blocks are shown separately for clarity, the actual implementation preferably involves a single application specific integrated circuit (ASIC) solution. The analyzer 10 is designed to extract and measure a pre-selected number of odd-numbered harmonics of the SAW signal, for example, one or more of the 1st, 3rd and 5th harmonics.

Block 12 is a SAW sensor device constructed in an oscillator configuration which includes a SAW oscillator. The SAW oscillator in block 12 defines a fundamental frequency which determines the frequencies of the selected harmonic which are extracted and measured. The analyzer 10 receives a SAW signal in the time domain from the SAW device 12 on line 13. The SAW signal is a first input to a mixer 14. A second input to the mixer 14 is from a programmable precision oscillator 28 on line 29. The operating frequency of the programmable precision oscillator 28 is selected by a spectral signal processing and control system 24, via line 27. The spectral signal processing and control system 24 advantageously selects the appropriate Nth harmonic frequency to be generated by the precision oscillator 28, for example, 1st harmonic at 250 MHz; 3rd harmonic at 750 MHz; or, 5th harmonic at 1250 MHz.

The mixed signal output on line 15 is filtered by a bandpass filter 16. The band-pass filtered signal on line 17 is amplified by a programmable amplifier 18, responsive to the spectral signal processing and control system 24 via line 25. The spectral signal processing and control system 24 controls the gain of the programmable amplifier such that, with no gas flowing over the SAW device, the signal power of all the selected harmonics are equal. The output of the programmable amplifier on line 19 is split and fed to each of a harmonic power measuring system 20 and a harmonic frequency measuring system 22. The harmonic power measuring system 20 measures the power content of each harmonic signal being measured. The harmonic frequency measuring system 22 measures the frequency shift of each harmonic signal being measured.

Data acquisition from the harmonic power measuring system 20 and from the harmonic frequency measuring system 22 is also performed by spectral signal processing and control system 24, via lines 21 and 23 respectively. Each data set includes the signal power of each of the harmonics measured, and the frequency difference between the precision oscillator 28 and the highest desired harmonic content in the SAW signal, in this example 1250 MHz. An algorithm that develops a harmonic signature from the above measurements to identify the chemical species and concentration is used to facilitate automatic processing and recognition. An optional implementation of the algorithm is in a back-propagation neural network 30, shown in dashed lines.

A number of data sets are acquired in a calibration mode using expected interfering gases. The resulting data is used to develop a baseline. In the detection mode, data sets acquired by the spectral signal processing and control system 24 are compared with the baseline to identify the gas of interest. In the more general case, base lines for interfering chemicals, radiation and other detectable phenomena can be identified to facilitate automatic recognition.

In the arrangement shown in FIG. 1, the higher order harmonics are generated and examined one at a time, and the examination need not be in any particular order. In accordance with the inventive arrangements, the harmonics can also be examined simultaneously, as shown in FIG. 4.

With reference to FIG. 4, an apparatus 100 for surface acoustic wave harmonic analysis provides for simultaneous analysis and measurement at the harmonics of interest. Each of the components in the analyzer 100 is the same as the corresponding component described in FIG. 1, except for the harmonic oscillator. Accordingly, the same reference numerals are utilized, except that reference numeral 28' denotes a programmable precision oscillator having multiple outputs for generating, for example, harmonics on each of lines 29a, 29b and 29c that are fixed harmonic multiples of the fundamental frequency of the SAW oscillator. The spectral signal processing and control system also generates control signals simultaneously, for example on lines 25a, 25b and 25c respectively, for setting the three programmable amplifiers shown. Each harmonic has its own processing path, including a mixer 14, a band-pass filter 16, a programmable amplifier 18 and harmonic power and frequency measuring systems 20, 22. The analyzer is also intended for implementation as an ASIC, and the spectral signal processing and control system can facilitate automatic operation by use of algorithms, such as implemented by optional neural network 30.

As an example of increased sensitivity obtained by the inventive arrangements, FIGS. 2 and 3 compare the respective frequency shifts for the fundamental frequency and 3rd harmonic of a 250 MHz SAW sensor, in which pre-humidified air is used as the test gas. FIG. 2 was obtained using the conventional method of measuring the frequency shifts of the fundamental frequency from the oscillator output of a SAW sensor in which the SAW device is connected in the feedback loop of the oscillator. FIG. 3 was obtained by measuring frequency shifts from the output of the harmonic frequency measuring system 22. In both figures the SAW sensor was coated with 0.25 mg/ml of polyethyleneimine (PEI), which selectively adsorbs water vapor. The vertical axes in both graphs is in Hertz, with each division equal to 100 KHz. The horizontal axes represent the acquisition time in minutes. The frequency change of the fundamental in FIG. 2 was about was about 160 KHz, between 0% relative humidity (R.H.) and 75% relative humidity. The frequency change of the higher order harmonic in FIG. 3 was about 370 KHz, between 0% relative humidity and 75% relative humidity. The much greater change in frequency of the harmonic in FIG. 3, by a factor of about 2, is clearly evident.

With regard to a methodology, the inventive arrangements provide for analysis not of the fundamental frequency, but higher order harmonic frequencies. In the presently preferred embodiments, these higher order harmonic frequencies are the 3rd and 5th order odd harmonics. The method not only utilizes harmonics of the SAW device to identify chemical species and gas concentration, for example, but can further use the complete spectral signature, including modulation changes.

A number of significant improvements result from this method and apparatus of the inventive arrangements, as compared to prior art SAW-based chemical sensors. First, the inventive arrangements allows the use of a microwave frequency for gas detection without actually having to fabricate a device using submicron lithographic techniques or resorting to costly electron-beam lithography. Second, the sensitivity of an acoustic wave gas sensor can be improved by at least a factor of two. Third, the detection limit of the absorbed chemical species can be improved by a factor of at least two. Fourth, the number of sensors required for mixtures can be reduced by a factor of x, where x is the number of harmonic amplitudes and/or frequency variables measured. Fifth, the inventive arrangements can always be used to optimize any SAW sensor device, independent of the fundamental operating frequency of the SAW device itself.

Accordingly, even if SAW device sensor sensitivity to chemical gases is increased by successfully fabricating a SAW device with a significantly higher fundamental frequency mode of operation, which is in any event now limited as a practical matter in prior art devices, such a higher-operating-frequency SAW device can always be optimized in accordance with the inventive arrangements taught herein.

What is claimed is:

1. A method for sensing and analyzing data with surface acoustic wave (SAW) devices, comprising the steps of:

propagating a sampling signal at a fundamental frequency through a SAW device coated for selective adsorption;

measuring at least one parameter of at least one higher order harmonic of said fundamental frequency sampling signal;

exposing said coated SAW device to enable said selective adsorption;

measuring said at least one parameter of said at least one higher order harmonic of said fundamental frequency sampling signal after said exposing step;

comparing said measurements of said at least one parameter of said at least one higher order harmonic before and after said exposing step; and, deriving a result of said selective adsorption based upon said comparing step.

2. The method of claim 1, wherein said at least one parameter is harmonic power.

3. The method of claim 2, wherein said at least one parameter is harmonic frequency.

4. The method of claim 1, wherein said at least one parameter is harmonic frequency.

5. The method of claim 1, wherein said at least one higher order harmonic is an odd-numbered harmonic.

6. The method of claim 1, wherein said at least one higher order harmonic is at least a 3rd harmonic.

7. The method of claim 1, wherein said at least one higher order harmonic is at least two of a 3rd harmonic and a 5th harmonic.

8. The method of claim 7, comprising the step of generating and measuring said at least two harmonics sequentially.

9. The method of claim 8, wherein said at least one parameter is at least one of harmonic power and harmonic frequency.

10. The method of claim 8, wherein said at least one parameter is harmonic power and harmonic frequency.

11. The method of claim 7, comprising the step of generating and measuring said at least two harmonics simultaneously.

12. The method of claim 11, wherein said at least one parameter is at least one of harmonic power and harmonic frequency.

13. The method of claim 11, wherein said at least one parameter is harmonic power and harmonic frequency.

14. The method of claim 1, wherein said comparing step is implemented with a neural network.

15. The method of claim 1, comprising the step of calibrating signal detection such that prior to said exposing step, all harmonics selected for generation and measurement have an equal signal power level.

16. An apparatus for sensing and analyzing data with surface acoustic wave (SAW) devices, comprising:
- a SAW device configured for operation with a SAW oscillator and coated for selective adsorption;
- an oscillator for generating at least one higher order harmonic of said SAW oscillator;
- a mixer for combining said at least one higher order harmonic and an output signal of said SAW device;
- a band-pass filter for said combined signal;
- a programmable amplifier for said band-pass filtered signal;
- a circuit for measuring at least one parameter of said amplified signal before and after said selective adsorption;
- an analyzer for comparing said measurements of said at least one parameter of said amplified signal before and after said selective adsorption and deriving from said comparing a result of said selective adsorption.

17. The apparatus of claim 16, wherein said oscillator and said programmable amplifier are controlled by said analyzer.

18. The apparatus of claim 17, wherein said measuring circuit measures at least one of harmonic power and harmonic frequency.

19. The apparatus of claim 18, wherein said oscillator generates at least two higher order odd harmonics of said fundamental frequency, each of which is measured before and after said selective adsorption, said analyzer deriving said result from a comparison of before and after measurements of said at least two higher order odd harmonics.

20. The apparatus of claim 19, wherein said at least two higher order odd harmonics are generated and measured sequentially.

21. The apparatus of claim 20, wherein said analyzer comprises a neural network.

22. The apparatus of claim 19, wherein said at least two higher order odd harmonics are generated and measured simultaneously.

23. The apparatus of claim 22, wherein said analyzer comprises a neural network.

24. The apparatus of claim 16, wherein said measuring circuit measures at least one of harmonic power and harmonic frequency.

25. The apparatus of claim 16, wherein signal detection is calibrated such that prior to said selective adsorption, all harmonics selected for generation and measurement have an equal signal power level.

* * * * *